US006645942B1

(12) United States Patent
Verma et al.

(10) Patent No.: US 6,645,942 B1
(45) Date of Patent: Nov. 11, 2003

(54) SOMATIC CELL GENE THERAPY

(75) Inventors: Inder Mohan Verma, Solana Beach, CA (US); Daniel Claude St. Louis, Gaithersburg, MD (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 08/232,452

(22) Filed: Apr. 22, 1994

Related U.S. Application Data

(63) Continuation of application No. 07/667,169, filed on Mar. 8, 1991, which is a continuation-in-part of application No. 07/187,214, filed on Apr. 28, 1988, now abandoned.

(51) Int. Cl.$^7$ .......................... A61K 31/70; C12N 5/00; A01N 63/00; A23P 1/00

(52) U.S. Cl. ...................... 514/44; 435/325; 424/93.21; 424/572

(58) Field of Search ............................. 424/93.21, 572; 435/240.2–325, 172.3, 948; 935/62, 70; 514/44

(56) References Cited

U.S. PATENT DOCUMENTS

| 4,497,796 A | 2/1985 | Salser et al. |
| 4,686,098 A | 8/1987 | Kopchick et al. |
| 4,868,116 A | 9/1989 | Morgan et al. |
| 4,980,286 A | 12/1990 | Morgan et al. |

FOREIGN PATENT DOCUMENTS

| WO | WO8700201 | 1/1987 |
| WO | WO8902468 | 3/1989 |

OTHER PUBLICATIONS

Axelrod et al. "Phenotypic correction of factor IX deficiency in skin fibroblasts of hemophilic dogs" *Proc. Natl. Acad. Sci. USA* 87:5173–5177.
Garver et al. "Production of glycolsylated physiologically "normal" human $\alpha_1$–antitrypsin by mouse fibrolasts modified by insertion of a human $\alpha_1$–antitrypsin cDNA using a retroviral vector" *Proc. Natl. Acad. Sci. USA* 84:1050–1054 (1987).
Miller, Dusty. "Progress Toward Human Gene Therapy" *Blood* 76(2):271–278 (1990).
Palmer et al. "Genetically modified skin fibroblasts persist long after transplantation but gradually inactivate introduced genes" *Proc. Natl. Acad. Sci. USA* 88:1330–1334 (1991).
Rosenberg et al. "Grafting Genetically Modified Cells to Damaged Brain: Restorative Effects of NGF Expression" *Science* 242:1575–1578 (1988).
Uckun et al. "Immunophenotype–karyotype Associations in Human Acute Lymphoblastic Leukemia" *Blood* 73(1) : 271–280 (1989).
Wolff et al. "Grafting fibroblasts genetically modified to produced L–dopa in a rat model of Parkinson disease" *Proc. Natl. Acad. Sci. USA* 86:9011–9014 (1989).
Bell et al., "Production of a tissue–like structure by contraction of collagen lattices by human fibroblasts of different proliferative potential in vitro", Proc. Natl. Acad. Sci. USA vol. 76:1274–1278 (1979).
Bell et al., "The Reconstitution of Living Skin", J. Investigative Dermatology vol. 81:2s–10s (1983).
Mann et al., "Construction of a Retrovirus Packaging Mutant and Its Uses to Produce Helper–Free Defective Retrovirus", Cell vol. 33:153–159 (1983).
Miller et al., "Expression of a Retrovirus Encoding Human HPRT in Mice", Science vol. 225:630–632 (1984).
Miller et al., "Infectious and Selectable Retrovirus Containing an Inducible Rat Growth Hormone Minigene", Science Vo. 225:993–998 (1984).
Williams et al., "Introduction of a new genetic material into pluripotent haematopoietic stem cells of the mouse", Nature vol. 310:476–480 (1984).
Miller et al., "Generation of Helper–Free Amphotropic Retroviruses That Transduce a Dominant–Acting, Methotrexate–Resistant Dihydrofolate Reductase Gene", Molecular and Cellular Biology vol. 5:431–437 (1985).
Verma, "Retroviral Vectors for Gene Transfer", Microbiology 1985, pp. 229–232.
Miller et al., "Transfer of Genes into Human Somatic Cells Using Retrovirus Vectors", Cold Spring Harbor Symposia on Quantitative Biology vol. LI:1013–1019 (1986).
Miller and Buttimore, "Redesign of Retrovirus Packaging Cell Lines To Avoid Recombination Leading to Helper Virus Production", Molecular and Cellular Biology vol. 6:2895–2902 (1986).
Anson et al., "Towards Gene Therapy for Hemophilia B", Mol. Biol. Med. vol. 4:11–20 (1987).

(List continued on next page.)

*Primary Examiner*—Deborah Crouch
*Assistant Examiner*—Joseph Woitach
(74) *Attorney, Agent, or Firm*—Stephen E. Reiter; Foley & Lardner

(57) ABSTRACT

The present invention is a somatic cell gene therapy method that is especially useful for the treatment of certain diseases that are caused by gene defects. According to the invention, fibroblast cells are transduced so that they express a "replacement" gene of interest. These transduced fibroblasts are preferably fixed in vitro in an extracellular matrix, and then implanted in the loose connective tissue of the skin of an individual or animal to be treated. Because the fibroblasts are implanted in a highly vascularized compartment of the skin i.e., loose connective tissue of the dermis, the transduced cells, and thus their "replacement" gene products, have direct access to the circulatory system. As a result the needed replacement gene products can easily and efficiently be distributed to other parts of the body. When the gene therapy is no longer needed, the implanted fibroblasts can be conveniently removed.

16 Claims, 5 Drawing Sheets

OTHER PUBLICATIONS

Gospodarowicz, "Isolation and Characterization of Acidic and Basic Fibroblast Growth Factor", Methods in Enzymology vol. 147:106–119 (1987).

Palmer et al., "Efficient retrovirus–mediated transfer and expression of a human adenosine deaminase gene in diploid skin fibroblasts from an adenosine deaminase–deficient human", Proc. Natl. Acad. Sci. USA vol. 84:1055–1059 (1987).

Garver et al., "Production of glycosylated physiologically "normal" human alpha1–antitrypsin by mouse fibroblasts modified by insertion of a human alpha1–antitryspin cDNA using a retroviral vector", Proc. Natl. Acad. Sci. USA vol. 84:1050–1054 (1987).

Selden et al., "Implantation of Genetically Engineered Fibroblasts into Mice: Implications for Gene Therapy", Science vol. 236:714–718 (1987).

Garver et al., "Clonal Gene Therapy: Transplanted Mouse Fibroblast Clones Express Human Alpha1–antitrypsin Gene in vivo", Science vol. 237:762–764 (1987).

Morgan et al., "Expression of an Exogenous Growth Hormone Gene by Transplantable Human Epidermal Cells", Science vol. 237:1476–1479 (1987).

St. Louis and Verma, "Whole Animal Gene Transfer", Current Communications in Molecular Biology, Cold Spring Harbor Laboratory Press, Miller and Calos editors, pp. 94–102 (1987).

St. Louis and Verma, "An alternative approach to somatic cell gene therapy", Proc. Natl. Acad. Sci. USA vol. 85:3150–3154 (1988).

SOMATIC CELL GENE THERAPY

This application is a continuation of application Ser. No. 07/667,169, filed Mar. 8, 1991, which is a continuation-in-part of Ser. No. 07/187,214, filed Apr. 28, 1988, now abandoned.

This application is a continuation-in-part application of Ser. No. 187,214, filed Apr. 28, 1988.

This invention was made with Government support under Grant No. CA 44360 awarded by the National Institutes of Health. The government has certain rights in the invention.

RELATED APPLICATIONS

FIELD OF THE INVENTION

The present invention relates generally to gene therapy. More specifically, the present invention relates to somatic cell gene therapy in humans and animals.

BACKGROUND OF THE INVENTION

Genetic defects in the human genome account for more than 4500 identified diseases. The resulting diseases are caused by single or multiple defects in a given gene. It is possible that many of these diseases can be alleviated, at least in part, if the deficient function can be supplied.

The concept of human gene therapy involves the introduction of a functionally active "replacement" gene into somatic cells of an affected subject to correct the gene defect. Retroviral vectors, because of their unique structure, modes of replication, and ability to infect a wide variety of cells, including stem cells, are ideally suited to transfer genetic material into somatic cells (Verma, 1985).

To ensure a life long supply of the replacement gene product, it is essential to introduce and express the functionally active gene in cells that proliferate during the entire adult life of the recipient. Because pluripotent stem cells in bone marrow have both self renewal capacity as well as the ability to give rise to all hematopoietic lineages, they are a popular target for the introduction of functionally active genes (Miller, et al., 1984; Williams, et al., 1984; Keller, et al., 1985; Dick, et al., 1985). Recently, hepatocytes have been used as target cells for introducing functionally active genes (Ledley, et al., 1987; Wolfe, et al., 1987).

Although the number of stem cells in adult marrow is low (0.01–0.1%), the use of high-titer retrovirus has ensured infection and gene delivery into these cells. The problem however has been that neither the foreign genes nor the retroviral vector introduced into these stem cells, the progenitor cells, or the mature end cells are efficiently expressed (Williams, et al., 1984; Joyner, et al., 1985).

Recently two groups used mouse fibroblasts to introduce and express foreign genes in mice (Selden, et al., 1987; Garver, et al., 1987b). One group implanted mice with a DNA transfected cell line and showed that the recipient mice made the gene product (growth hormone) but maintained the graft only if the mice were immunosuppressed (Selden, et al., 1987). The other group, using a chimeric retroviral vector containing the alpha$_1$-antitrypsin gene, produced a cell line from a transduced cell and then transplanted cells from the line into the peritoneal cavity of nude mice (Garver, et al., 1987b). In both cases, cell lines were generated that would potentially be tumorigenic in mice. Neither study addresses the issue of cell maintenance in grafted mice without the use of harsh immunosuppressive agents.

In addition to the work that has been done with fibroblasts, at least one group has shown that retroviral-mediated gene transfer can be used to introduce a recombinant human growth hormone gene into cultured human keratinocytes (Morgan, et al., 1987). The transduced keratinocytes secreted biologically active growth hormone into the culture medium. When grafted as an epithelial sheet onto athymic mice, these cultured keratinocytes reconstituted an epidermis that was similar in appearance to that produced by normal cells, but from which human growth hormone could be extracted. Unfortunately, it was not possible to determine the rate of diffusion of human growth hormone from the graft site to the bloodstream. This may have been due to the fact that the surface skin graft does not efficiently vascularize.

SUMMARY OF THE INVENTION

The present invention discloses a new gene therapy method based on the use of transduced fibroblasts that are implanted in the loose connective tissue of the skin of the subject to be treated. According to the invention, transduced fibroblasts are preferably created by infecting fibroblast cells in vitro with chimeric retroviruses that contain at least one functionally active "replacement gene", i.e., foreign or exogenous genetic material that does not normally occur in fibroblast cells, or if it does, is not expressed by the fibroblast cells in biologically significant concentrations. Expression of "replacement gene" can be maintained under the control of the long terminal repeat (LTR) of the retroviral vector and/or under the control of constitutive or inducible exogenous sequences. The transduced fibroblasts are then preferably fixed by culturing them in vitro in an extracellular matrix. Finally, the transduced fibroblasts are implanted subcutaneously in the loose connective tissue of the skin of the individual or animal being treated. To insure rapid vascularization of the implanted fibroblasts, an angiogenic substance such as a fibroblast growth factor is preferably placed in the loose connective tissue along with the implant. Because the fibroblasts are implanted in a highly vascularized compartment of the skin i.e., loose connective tissue of the dermis, the transduced cells, and thus their "replacement" gene products, have direct access to the circulatory system. As a result, the needed replacement gene products can easily and efficiently be distributed to other parts of the body. When the gene therapy is no longer needed, the implanted fibroblasts can be conveniently removed.

To overcome the prior art problem of inefficient expression, the present invention discloses an alternative strategy for somatic cell gene transfer. The new strategy uses skin fibroblasts that are infected with chimeric retrovirus containing a functionally active endogenous or foreign "replacement" gene. Once infected with the chimeric retrovirus, the transduced fibroblasts are preferably "fixed" in an extracellular collagen matrix, and then implanted in the loose connective tissue of the skin. Since this compartment of the dermis is highly vascularized, the transduced fibroblasts, and thus their "replacement" gene products, have direct access to the circulatory system. As a result, the needed replacement gene products can easily and efficiently be distributed to other parts of the body.

The method described herein obviates the need for established cell lines and instead uses fibroblast cells from recipient subjects. Use of a subject's own cells minimizes the possibility of rejection. In addition, culturing the cells in an extracellular collagen matrix circumvents the problem of necrosis that would ensue following subcutaneous injection (Bell, et al., 1983). Finally, the high efficiency of retroviral infection and expression in fibroblasts (80%) essentially eliminates the need to identify transduced cells by means of selectable markers, thus greatly simplifying the overall endeavor of introduction of foreign genes.

Clinical disease states that are candidates for the gene therapy treatment method of the present invention include hemophilia, endocrine deficiency, alpha$_1$-antitrypsin, birth control, etc.

DETAILED DESCRIPTION OF THE INVENTION

Figure 1:
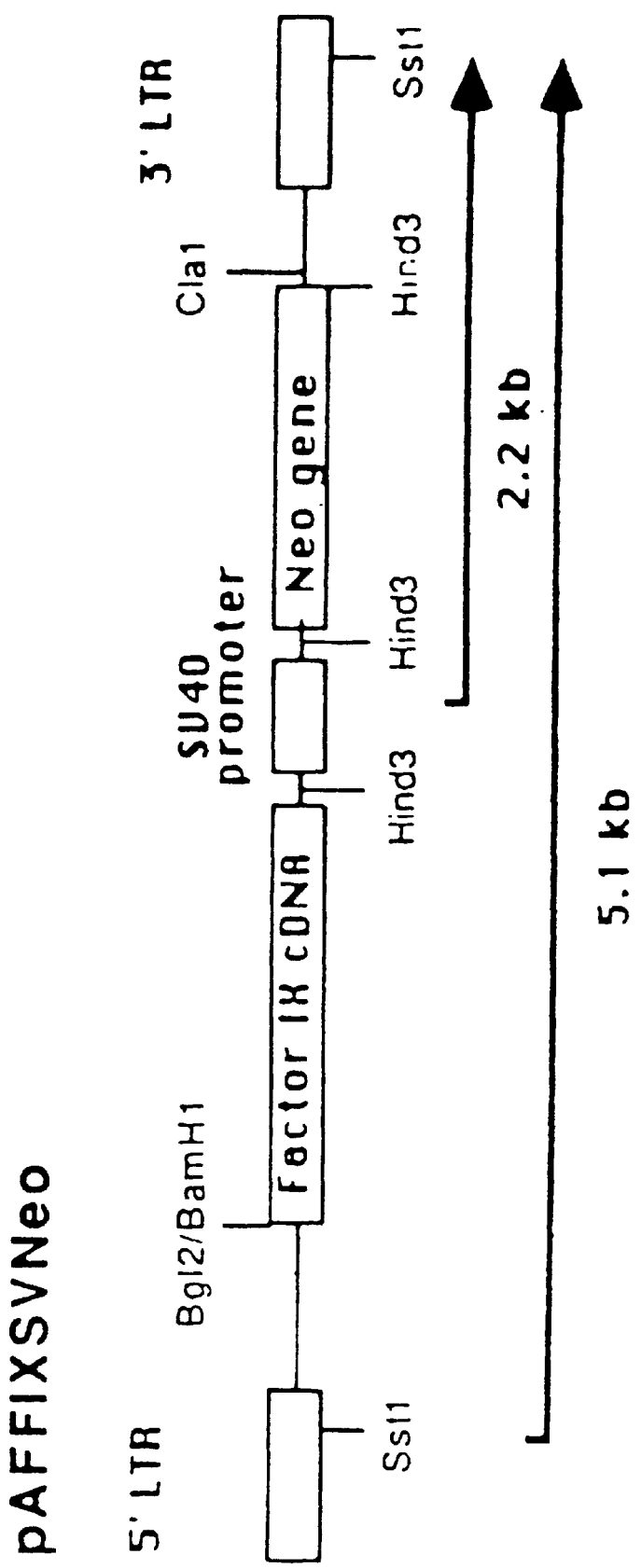
FIG. 1 is a schematic drawing of the structural arrangement of the recombinant factor IX retrovirus pAFFIXSV-Neo.

The present invention is based on the discovery that transduced skin fibroblasts can be used for somatic cell gene therapy when the transduced fibroblasts are fixed in vitro in an extracellular collagen matrix and implanted in the loose connective tissue of the dermis of a subject to be treated. The discovery makes it possible to overcome several problems that have been encountered when prior art gene therapy methods were used to treat animals or individuals with genetic defects. Such problems include: (1) inefficient expression of the foreign "replacement" genes (Williams, et al., 1984; Joyner, et al., 1985); (2) use of transduced cells that had the potential to be tumorigenic to the animal or individual being treated (Selden, et al., 1987; Garver, et al., 1987b); (3) use of harsh immunosuppressive agents to avoid rejection by the animal or individual being treated (Selden, et al., 1987); (4) necrosis following subcutaneous injection of cells (Bell, et al., 1983); and (5) poor diffusion of the replacement gene product (Morgan, et al., 1987). As will be discussed more fully below, the present invention preferably employs chimeric retroviruses to introduce replacement genes into skin fibroblasts. Because of the high efficiency of retroviral infection and expression in fibroblasts, the present invention essentially eliminates the need to use marker genes to identify transduced cells. This greatly simplifies the overall problem of introducing replacement genes into cells that will be used for gene therapy. Since the invention preferably uses fibroblast cells from recipient individuals, it obviates the need to use potentially tumorigenic cell lines. Use of skin fibroblasts from the subject to be treated minimizes the possibility of rejection, which in turn lessens the need for harsh immunosuppressant drugs. In addition, since the invention uses transduced fibroblasts that preferably have been fixed in vitro in an extracellular collagen matrix, the problem of necrosis is also minimized. Finally, since the invention implants the transduced fibroblasts into the highly vascularized loose connective tissue of the dermis, the replacement gene products are easily and efficiently distributed to other parts of the body.

In the present specification and claims, reference will be made to phrases and terms of art which are expressly defined for use herein as follows:

"LTR" means long terminal repeat;

"factor IX" refers to the blood clotting factor gene or protein of the same name;

"pAFVXM" refers to a retroviral construct generated by Kriegler, et al., (1984). pAFVXM is a progenitor construct for the recombinant factor IX retrovirus, pAF-FIXSVNeo. A replacement gene of interest (or a cDNA for such a gene) can be linked directly to the 5' LTR in the retrovirus by inserting a BamHI/HindIII fragment from the gene or clone between the BglII/HindIII sites of pAFVXM (Anson, et al., 1984);

"pKoNeo" is a neomycin phosphotransferase expression plasmid;

when reference is made herein to the Greek letter "psi" (ψ), the word psi -is sometimes substituted for the symbol ψ;

the letter "g" is sometimes used herein to signify the symbol for the Greek letter "gamma", γ;

"MEF" means primary mouse embryo fibroblasts;

"Bl/6" refers to an immortalized skin cell line derived from x-ray irradiated skin fibroblasts obtained from C57BL/6J mice;

"psiFIXNeo" means the cell line ψFIXNeo;

"moi" means multiplicity-of-infection;

"POLYBRENE" is the trademark of Sigma Chemical Company, St. Louis, Mo., for 1,5,-Dimethyl-1,5-diazaundecamethylene polymethobromide; also referred to as Hexadimethrine bromide;

"DMEM" means Dulbecco's modified Eagle's medium, which is substantially the same as Dulbecco-Vogt modified Eagle's medium;

"ELISA" means enzyme linked immunoabsorbant assay;

"FGF" means fibroblast growth factor. FGF is an angiogenic substance that can be used in the present invention to stimulate vascularization of the implanted fibroblasts;

"transduction" refers to the process of conveying or carrying over, especially the carrying over of a gene from one cell to another by a virus or retrovirus. A retrovirus that carries a gene from one cell to another is referred to as a transducing chimeric retrovirus. An eukaryotic cell that has been transduced will contain new or foreign genetic material (e.g., a replacement gene) in its genome as a result of having been "infected" with the chimeric transducing retrovirus;

"transfection of eukaryotic cells" is the acquisition of new genetic material by incorporation of added DNA;

"skin" refers to the body's largest organ. Skin consists of two components, the epidermis and the dermis. The dermis is a relatively inert structure which consists of collagen and other matrix materials. The epidermis lies above the dermis and is separated from it by a basement membrane;

"fibroblasts" refers to flat, elongated connective tissue cells with cytoplasmic processes at each end and an oval, flat nucleus. Fibroblasts, which differentiate into chondroblasts, collagenoblasts, and osteoblasts, form the fibrous tissues in the body, e.g., tendons, aponeuroses, plus supporting and binding tissues of all sorts. Like other cells in the body, fibroblasts carry an entire complement of genetic material. However, only a small percentage of the genes contained in fibroblasts are biologically functional; that is, most of the genes in fibroblasts are not expressed at all or are expressed at such low levels that the proteins they encode are produced in undetectable amounts or at concentrations which are not biologically functional or significant. Using routine methods of molecular biology it is now possible to introduce exogenous genetic material (i.e., replacement genes) into mammalian cells, thus enabling them to express genetic materials not normally expressed. The transduced fibroblasts of the present invention incorporate exogenous genetic material, which they express, thereby producing the gene product encoded by tue incorporated exogenous genetic material;

a "promoter" is a specific nucleotide sequence recognized by RNA polymerase, the enzyme that initiates RNA synthesis. When exogenous genes are introduced into fibroblasts using a retroviral vector, the exogenous genes are subject to retroviral control; in such a case, the exogenous gene(s) is transcribed from an endogenous retroviral promoter. It is possible to make retroviral vectors that, in addition to their own endogenous promoters, have exogenous promoter elements which are responsible for the transcription of the exogenous gene(s). Such exogenous promoters include constitutive and inducible promoters. Constitutive promoters are promoters that control the expression of gene functions that are needed in virtually all cell types. Sustained expression of genes under the control of constitutive promoters occurs under all conditions of cell growth, and does not require the presence of a specific substrate to induce gene expression. Conversely, expression of genes controlled by inducible promoters is responsive to the presence or absence of an inducing agent. For example, it is possible to make a construct in which there is an additional promoter that is always on, so long as the cell maintains its viability. Alternatively, one can employ a construct modulated by an external factor or cue, and in turn to control the level of exogenous protein being produced by the fibroblasts by activating the external factor or cue. As an illustration, the promoter for a gene which encodes certain constitutive or "housekeeping" functions, such as, for example, hypoxanthine phosphoribosyl transferase (HPRT), dihydrofolate reductase (DHFR), adenosine deaminase, phosphoglycerol kinase (PGK), pyruvate kinase, phosphoglycerol mutase, and the like, will be continuously expressed. Alternatively, the gene which encodes the metal-containing protein metallothionein is responsive to $Cd^{++}$ ions. Incorporation of any one of the above-described promoters makes it possible to either continuously produce the protein of interest, or to regulate the production of the proteins produced by the transduced fibroblasts of the invention;

"subcutaneously" means below the basement membrane of the epidermis (abbreviated as "s.c.");

"i.p." means intraperitoneally;

"skin fibroblasts" are fibroblast cells that are normally found in the dermis portion of the skin;

"syngeneic" means isogeneic, i.e., having the same genetic constitution;

"exogenous" genetic material means DNA or RNA, either natural or synthetic, that is not naturally found in cells of a particular type; or if it is naturally found in the cells, it is not expressed in these cells in biologically significant levels. For example, a synthetic or natural gene coding for human insulin would be exogenous genetic material to a yeast cell since yeast cells do not naturally contain insulin genes; a human insulin gene inserted into a skin fibroblast cell would also be an exogenous gene to that cell since skin fibroblasts do not express human insulin in biologically significant levels;

"exogenous" genetic material and "foreign" genetic material, as used herein, mean the same thing; and the terms "exogenous" and "foreign", when used to describe genes or genetic materials, are used interchangeably herein;

"retroviral vectors" are the vehicles used to introduce replacement genes into the skin fibroblasts. The following paragraphs contain some general background information about retroviruses.

Retrovirus are RNA viruses; that is, the viral genome is RNA. This genomic RNA is, however, reverse transcribed into a DNA intermediate which is integrated very efficiently into the chromosomal DNA of infected cells. This integrated DNA intermediate is referred to as a provirus.

The retroviral genome and the proviral DNA have three genes: gag, pol and env, which are flanked by two long terminal repeat (LTR) sequences. The gag gene encodes the internal structural (nucleocapsid) proteins; the pol gene encodes the RNA-directed DNA polymerase (reverse transcriptase); and the env gene encodes viral envelope glycoproteins. The 5' and 3' LTRs serve to promote transcription and polyadenylation of virion RNAs.

Adjacent to the 5' LTR are sequences necessary for reverse transcription of the genome (the tRNA binding site) and for efficient encapsidation of viral RNA into particles (the ψ or psi site). (Mulligan, 1983; Mann et al., 1983; Verma, 1985.)

The various elements required for replication of the retrovirus can be divided into cis- and trans-acting factors. The trans-acting factors include proteins encoded by the viral genome, which are required for encapsidation of viral RNA, entry of virions into cells, reverse transcription of the viral genome, and integration of the DNA form of the virus (i.e., the provirus) into host DNA. The cis-acting factors include signals present in the viral RNA which interact with the above-described proteins and other factors during virus replication.

If the sequences necessary for encapsidation (i.e., packaging of retroviral RNA into infectious virions) are missing from the viral genome, the result is a cis defect which prevents encapsidation of genomic RNA. The resulting mutant is however still capable of directing synthesis of all virion proteins. When the packaging signals are removed, viral RNA and proteins are still synthesized, but no infectious particles are made because viral RNA cannot be packaged into virions. Mann, et al., (1983) used this strategy to create ψ2 cell lines which supported the generation of infectious transducing retroviruses without generating helper murine leukemia viruses. Unfortunately, murine leukemia virus env gene product is only able to infect rodent cells, which limits the utility of ψ2 cell lines. On the other hand, amphotrophic murine retroviruses are able to infect a wide variety of cell types, including human cells.

Using a strategy similar to the one described by Mann, et al., for the production of the ψ2 cell lines, Verma and his colleagues generated a cell line using the env gene product of the amphotrophic viruses (Verma, 1985; Miller, et al., 1985; Miller, et al., 1986). As a result of this work, a wide-host-range, packaging defective system was made available for the generation of high-titer retroviruses containing exogenous genes (Verma, 1985; Miller, et al., 1985; PCT Internat'l. Applic. PCT/US85/01442). Such retroviruses, or retroviral vectors, have general utility for high-efficiency transduction of genes in cultured cells, and specific utility for use in the method of the present invention.

With regard to the fibroblasts employed herein, preferably they will be skin fibroblasts from the animal or individual to be treated with the gene therapy. Fibroblasts from these subjects can easily be obtained by skin biopsy, and then maintained in culture until it is convenient to transduce them. General methods for maintaining fibroblast cells in culture are well known to those skilled in the art of tissue culture. Such methods include culturing the cells in Dulbecco-Vogt modified Eagle's medium with 10% fetal bovine serum. Such known methods can be used by the skilled artisan, without undue experimentation, to culture the fibroblast cells prior to transduction. See generally, the Materials and Methods sections of Palmer, et al., (1987).

Exogenous genetic material or genes especially useful in the invention are preferably those genes that encode secretory proteins. Such useful genes include, but are not limited to, genes that encode blood clotting factors such as human factors VIII and IX; hormone genes such as the genes encoding for insulin, parathyroid hormone, luteinizing hormone releasing factor (LHRH), alpha and beta seminal inhibins, and human growth hormone; enzyme genes; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as $alpha_1$-antitrypsin, and genes encoding substances that function as drugs, e.g., genes encoding the diphtheria and cholera toxins. Genes that encode useful "gene therapy" proteins, e.g., many enzyme proteins, that are not normally secreted can be used in the invention if they are "functionally appended" to a signal protein sequence that will "transport" them across the fibroblasts' limiting membranes and into the extracellular space. A variety of such signal sequences are known and can be used by those skilled in the art without undue experimentation.

It is possible to use vehicles other than retroviruses to genetically engineer the fibroblasts of the present invention. However, chimeric retroviruses are the preferred agents used to incorporate new genetic material into the skin fibroblasts. Retroviruses and helper-free replication-defective viral vectors are well known and can be adapted for use in the present invention without undue experimentation. Examples of such retroviruses are disclosed in the Experimental Section of present specification; additional examples are disclosed and discussed in Palmer, et al., (1987); Miller, et al., (1986); St. Louis and Verma (1987); Miller, et al., (1985); and in PCT Patent Application No. PCT/US85/01442 which has been assigned to the Salk Institute for Biological Studies, San Diego, Calif. Helper-free replication-defective viral vectors that have a dominant selectable marker such as the neomycin resistance gene or the mutant DHFR gene (Miller, et al., 1985) can be used in the present invention. However, since the efficiency of retroviral infection is about 80%, use of a dominant selectable marker to identify transfected cells is usually not necessary.

It is possible, through the use of a recombinant retrovirus, to introduce new genetic material into fibroblasts without altering the functional characteristics of the recipient fibroblasts. Therefore, retroviral vectors useful in the method of the present invention will have a cloning site. The presence of such a site makes it possible to introduce exogenous genetic material into the vector and have it expressed by fibroblasts co-cultivated with the recombinant virus. Methods for introducing exogenous genetic material into the retroviral vectors are known and can be used by the skilled artisan without undue experimentation. For example, useful methods are disclosed in the Experimental Section of this specification and in Palmer, et al., (1987). (In Palmer, et al., 1987, see especially the Materials and Methods section of the publication.) Additional methods and helpful details are disclosed in Verma, (1985); Miller, et al., (1985); Miller, et al., (1986); St. Louis and Verma, (1987), and in PCT Patent Application No. PCT/US85/01442 which has been assigned to the Salk Institute for Biological Studies, San Diego, Calif.

A cell line that produces recombinant amphotropic chimeric retrovirus is used in co-cultivation with the fibroblasts to be "transduced". The ψam cell line, which can be modified using standard techniques to include chimeric retrovirus, is available from the American Type Culture Collection, Rockville, Md. For example, a ψam line which produces a chimeric retrovirus can be constructed as follows: the exogenous gene or cDNA of interest is ligated into a cloning site in the retroviral vector. (Such a vector could also carry a selectable marker such as the Neo gene.) Chimeric retroviruses that carry the exogenous gene or DNA of interest are isolated and transfected into ψam cells. ψam cells that produce the chimeric virus construct are isolated, e.g., as G418 resistant colonies if the chimeric retrovirus carried the Neo gene as a selectable marker.

Co-cultivation methods are well known to those skilled in the art and can be used in the present invention without undue experimentation. Generally, the methods can be summarized as follows: On day one, fibroblast cells to be "infected" with chimeric retrovirus are seeded in conventional culture medium at approx. $5 \times 10^6$ cells per 60-mm culture dish. On day two, the culture medium is replaced with medium from cells that produce chimeric retrovirus. On day three, the infected fibroblasts are suspended with an enzyme such as trypsin. (Although it would not usually be necessary due to the high efficiency of bulk infection, if the chimeric retrovirus carried a selectable marker, the fibroblast cells would be grown in culture dishes containing selective media. Resistant colonies (i.e., those formed from cells that have been transduced by the chimeric retrovirus) would then be scored after an appropriate amount of time (10–12 days). Fibroblasts from the resistant colonies would contain the new genetic material carried by the transducing chimeric retroviruses.

According to the invention, once the skin fibroblasts have been transduced with chimeric retrovirus, they are preferably "fixed" in vitro in an extracellular matrix. See generally, Elsdale, et al., (1972) and Bell, et al., (1979). A preferred method for "fixing" the transduced fibroblasts in vitro in an extracellular matrix is discussed in the Experimental Section of this specification. In summary, the fibroblasts are preferably fixed by culturing them in an extracellular matrix composed of collagen (either natural or synthetic) and culture medium. The cells are cultured at about 37° C. for about 3 days, during which time the collagen contracts to a tissue-like structure. Once contracted, the "artificial" fibroblast tissue grafts can be implanted into the loose connective tissue in the dermis of the recipient subject. While the extracellular collagen matrix is preferred (since it is easy, inexpensive and effective), those skilled in the art will realize that other collagen-like materials, both natural and synthetic, could be used to generate the extracellular matrix into which the transduced fibroblasts become fixed.

To ensure rapid vascularization of the grafted implant, it is preferable to insert basic fibroblast growth factor along with each graft. The growth factor can be conveniently supplied by first applying it to a piece of sterile sponge, e.g., as gelfoam (Upjohn), which is then implanted in the connective tissue along with each graft.

The present invention makes it possible to genetically engineer skin fibroblasts that can secrete a variety of useful gene products (e.g., clotting factors, immunoregulatable factors, hormones and drugs). When these transduced fibroblasts are implanted into the dermis of an individual or animal, the secreted gene products diffuse into the bloodstream, and thus are carried to various parts of the body.

The implanted transduced fibroblasts of the present invention can be used in a variety of applications. For example, the implanted fibroblasts can serve as a continuous drug delivery system to replace present regimes that require periodic administration (by ingestion, injection, etc.) of a needed substance (e.g., to provide continuous delivery of insulin). This would be very useful since it would eliminate the need for daily injections of insulin.

Genetically engineered fibroblasts can also be used for the production of clotting factors. Hemophiliacs lack a protein called Factor VIII, which is involved in blood clotting. Factor VIII is now administered by injection. Like insulin, it could be made continuously or inducibly by transduced fibroblasts. Similarly, transduced and implanted fibroblasts could also be used to deliver growth hormone.

Another application for transduced fibroblasts produced by the present invention is in fertility control. Several hormones, including luteinizing hormone releasing factor (LHRH) and the seminal and ovarian inhibins, are being studied for their ability to regulate fertility. Continuous administration of LHRH results in a sterile individual; yet when administration of the hormone is stopped, fertility returns. Rather than taking LHRH injections or oral medication, one could implant collagen fixed fibroblasts carrying the LHRH gene under the control of a constitutive promoter, and thus provide a continuous supply of the hormone.

In yet another application for transduced fibroblasts produced by the process of the present invention, lymphokines such as GM-CSF can be continuously delivered to boost a subject's immune competence. Such treatment is especially useful in situations where the subject's immune system has been compromised by disease or treatment, such as in chemotherapy.

In each of the cited applications for the transduced fibroblasts of the present invention, the amount of replacement gene product delivered to the subject can be controlled by controlling such factors as: (1) the type of promoter used to regulate the replacement gene (e.g., use of a strong promoter or a weak one); (2) the nature of the promoter, i.e., whether the promoter is constitutive or inducible; (3) the number of transduced fibroblasts that are present in the implant; (4) the size of the implant; (5) the number of implants, (6) the length of time the implant is left in place, etc.

Without further elaboration, it is believed that one of ordinary skill in the art can, using the preceding description, and the following Experimental Section, utilize the present invention to its fullest extent. The material disclosed in the Experimental Section is disclosed for illustrative purposes and therefore should not be construed as limiting the appended claims in any way.

EXPERIMENTAL SECTION

Mouse primary skin fibroblasts were infected with a recombinant retrovirus containing human factor IX cDNA. Bulk infected cells capable of synthesizing and secreting biologically active human factor IX protein were embedded in collagen and the implant grafted under the epidermis. Sera from the transplanted mice contain human factor IX protein for at least 10–12 days. Loss of immunoreactive human factor IX protein in the mouse sera is not due to graft rejection. Instead, the mouse serum contains anti-human factor IX antibodies, which react with the protein.

EXAMPLE I

A. Construction and Infection by Recombinant Factor IX Retroviruses

The recombinant pAFFIXSVNeo is based on a retroviral construct pAFVXM generated by Kriegler, et al. (Kriegler, et al., 1984). A human factor IX cDNA was linked directly to the 5' long terminal repeat (LTR) by inserting a 1.6 kilobase (kb) BamHI/HindIII fragment from the clone CVI between the BglII and HindIII sites of pAFVXM (Anson, et al., 1984). The entire expression unit from the neomycin phosphotransferase expression plasmid (pKoNeo) was excised by partial HindIII digestion and inserted into the HindIII site of the above factor IX viral construct (FIG. 1; in the figure, arrows indicate transcripts that initiate at either the promoter located in the 5' LTR, or the simian virus 40 early promoter located between the two LTRs, and terminate at the polyadenylation signal in the 3' LTR; vertical bars indicate the putative initiation site of transcription; the restriction endonuclease cleavage sites SstI, HindIII, BamHI, BglII and ClaI are diagnostic sites used during the construction of the vector or subsequent characterization of the provirus in the genome of infected cell lines).

"Helper free" recombinant ecotropic virus in $\psi 2$ cells was generated as described (Miller, et al., 1986; Mann, et al., 1983). The titres of recombinant retrovirus expressed from drug resistant clones were done essentially as described (Miller, et al., 1986).

Primary mouse embryo fibroblasts (MEF) were obtained from day 17 embryos of C57BL/6J mice (Todaro, et al., 1963). The BL/6 line is an immortalized skin cell line derived from x-ray irradiated skin fibroblasts obtained form C57BL/6J mice. The skin fibroblast cell line BL/6, and NIH3T3 TK$^-$ cells were infected with recombinant retroviruses from the cell line, $\psi$FIXNeo 4, at a multiplicity-of-infection (moi) of 1–2 in the presence of POLYBRENE at 8 $\mu$g/ml; MEF cells were infected at a moi of 5.

B. Implantation of Infected Mouse Fibroblasts in Mouse

Infected BL/6 and MEF cells were cultured in vitro in an extracellular matrix composed of rat tail type I collagen (1 mg/ml; Sigma) and Dulbecco's modified Eagle's medium (DMEM) supplemented with 10% fetal bovine serum in a 5-cm dish (Elsdale, et al., 1972; Bell, et al., 1979). The cells were cultured at 37° C. for 3 days during which the collagen lattice contracted to a tissue-like structure (1/25th the area of the original gel). Once contracted, two artificial tissues containing approximately $4 \times 10^6$ infected fibroblasts were grafted into the loose connective tissue of the dermis in the mid-back of a recipient C57BL/6 mouse. To ensure rapid vascularization of the grafted tissue, a 2-mm2 piece of gelfoam (Upjohn) containing 2 $\mu$g of basic fibroblast growth factor was inserted into the loose connective tissue along with each graft. Serum samples were drawn at two day intervals and analyzed for the presence of human factor IX by ELISA.

C. Analysis of Secreted Factor IX

Levels of antigenic factor IX were assayed by ELISA as described by Anson, et al., (1987). Biologically active human factor IX was immunoaffinity purified using A7 antibody (Anson, et al., 1987; Smith, et al., 1987). The amount of biologically active protein was determined by a one step clotting assay using canine factor IX deficient plasma (Goldsmith, et al., 1978). This assay is based on the ability of the sample to decrease the prolonged activated partial thromboplastin time of congenital factor IX-deficient plasma. Purified human factor IX was used as a control.

EXAMPLE II

A. Transduction of Neomycin Resistance and Expression of Human Factor IX

The titres of helper-free ψFIXNeo virus produced in the various cell lines ranged from $3\times10^5$ to $7\times10^5$ G418 resistant colony forming units per ml when assayed by NIH3T3 TK⁻ cells. As measured by ELISA, all of the virus producing cell lines secreted essentially the same levels of factor IX into the culture media (approx. 200 ng/ml). All infected and drug resistant cell lines were also found to secrete factor IX into the culture media, albeit at different levels (see FIG. 2; showing the rate of secretion of human factor IX by the virus producing cell line ψFIXNeo 4 (open squares) and by infected NIH3T3 TK⁻ cells (solid squares), BL/6 cells (solid diamonds), and MEF cells (open diamonds); cells were seeded at $3\times10^6$ cells per 5 cm dish in 4 ml of medium; at each indicated time point 100 μl of medium was removed and assayed for human factor IX by enzyme linked immunoabsorbant assay (ELISA) (Anson, et al., 1987); the mouse anti-human monoclonal antibody, FXC008, generated by Bajaj, et al. (1985) was used as the primary antibody, whereas pooled normal human sera were used as a standard; each time point was done in triplicate and thus represents an average amount of factor IX secreted over a 48 hr period; curves were corrected for the slight increase in cell number over this period).

The organization of the integrated recombinant retrovirus in the virus producing cell line was determined by Southern blot analysis of SstI digested genomic DNA isolated from either uninfected or infected ψFIXNeo 4, NIH3T3 TK⁻, BL/6, and MEF cells, fractionated by agarose gel electrophoresis, transferred onto a nitrocellulose membrane and hybridized to either a nicktranslated 1.6 kb factor IX cDNA probe, or 1.4 kb HindIII to BamHI Neo DNA probe; under hybridization conditions, human factor IX cDNA does not hybridize to mouse DNA). SstI cleaves once in each LTR to generate a 5.1 kb DNA fragment. All infected cells displayed a single band of the expected size of approximately 5.1 kb which hybridizes to both the factor IX cDNA and the Neo probe, therefore ruling out any detectable rearrangements. Furthermore, the size of this band in infected NIH3T3 TK⁻, BL/6, and MEF cells is identical to that found in the virus producing cell line ψFIXNeo 4.

The RNA blot analysis (of the RNA-isolated from ψFIXNeo 4, infected NIH3T3 TK⁻, BL/6 and MEF), when hybridized to factor IX probe, shows only one major transcript of the expected size of 5.1 kb, corresponding to full length viral RNA could be detected in the infected cells. Hybridization with Neo probe reveals an additional 2.2 kb transcript that is the predicted size of the mRNA species, the synthesis of which is initiated from the simian virus 40 early promoter and is terminated in the 3' LTR. Ratios of the steady state levels of the 5.1 kb and the 2.2 kb transcripts varied within the different infected cell types. From these results, it is concluded that the ψFIXNeo recombinant retrovirus is properly integrated and expressed in the infected cells.

B. Secretion of Factor IX Protein

Figure 2:
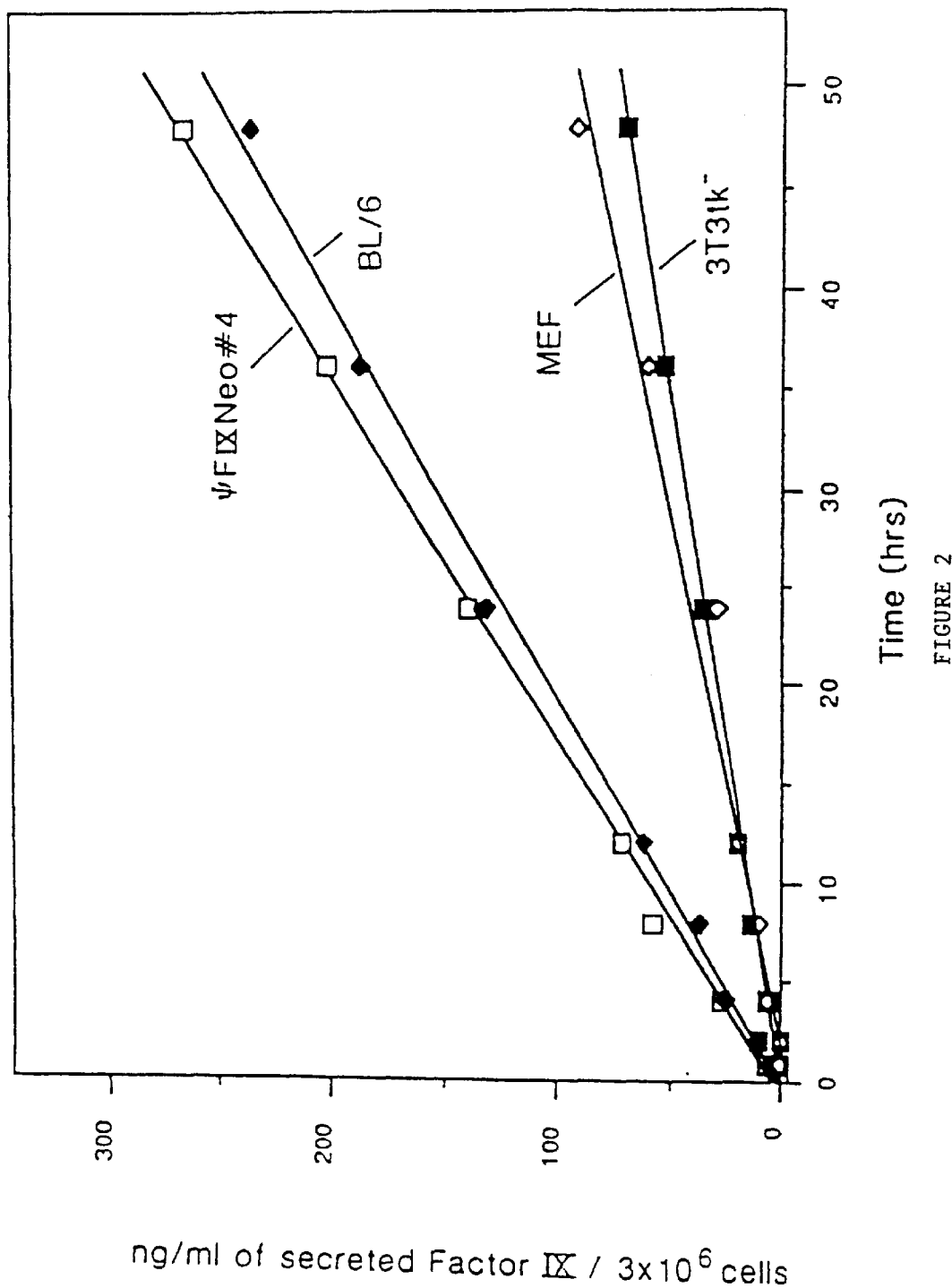
FIG. 2 is a graph that illustrates secretion of human factor IX.

Because human factor IX is a secretory protein, it was important to verify if it is secreted into the medium of the infected cells. FIG. 2 shows that both rate and extent of antigenic factor IX released into the medium is dependent on the cell type rather than on the relative amounts of the factor IX transcripts. For instance, steady state levels of factor IX transcript in infected NIH3T3 TK⁻ cells is much higher than in BL/6 cells; yet the rate and amount of factor IX secreted in the latter cell type is much higher. Both the virus producing cell line ψFIXNeo 4 and infected skin fibroblast cell line BL/6, secreted antigenic factor IX at similar rates, approximately 5.7 ng per ml/hr for $3\times10^6$ cells and 5.0 ng per ml/hr for $3\times10^6$ cells, respectively. This rate was almost 3 fold higher than the rate of factor IX secretion seen for infected MEF (1.75 ng per ml/hr for $3\times10^6$ cells) and infected NIH3T3 cells (1.65 ng per ml/hr for $3\times10^6$ cells). These results indicate that the rate of synthesis and/or secretion may be a property of the cell type, rather than the levels of expression.

C. Secreted Human Factor IX Protein Is Biologically Active

The primary translation product of factor IX gene undergoes extensive post-translational modification which include addition of sialic carbohydrates (Chavin, et al., 1984; Fournel, et al., 1985), vitamin K-dependent conversion of glumatic acid residues to γ-carboxy/glutamic acid (Suttie, 1980) and β-hydroxylation of aspartic acid residue 64 (Ferlund, et al., 1983). The γ-carboxylation of factor IX is essential for clotting activity and this modification generally occurs in the liver, the primary source of factor IX synthesis in the body.

Two different approaches were taken to assess biological activity of human factor IX secreted from cells in culture:

(i) In the first approach, infected mouse embryo fibroblasts were cultured in factor IX deficient canine serum obtained from hemophiliac dogs, supplemented with epidermal growth factor (10 ng/ml) and vitamin K (25 ng/ml). Media harvested after 48 hr incubation was monitored for activity by a one step assay (Goldsmith, 1978). Conditioned media from MEF cells contained biologically active human factor IX at 210 ng/ml which is similar to the levels seen with ELISA assays;

(ii) In the second approach, based on the fact that BL/6 cells did not attach to the tissue culture dish in canine sera, a different approach was taken. Infected BL/6 cells were grown in 10% total calf serum supplemented with vitamin K (25 ng/ml). Media harvested after 48 hr incubation was applied to an immunoaffinity column containing human factor IX monoclonal antibody A-7 (Anson, et al., 1987; Smith, et al., 1987). This monoclonal antibody recognizes the calcium binding domain of human factor IX protein, thus discriminating between carboxyl-lacking factor IX and biologically active γ-carboxyl human factor IX. One-hundred and sixty ml of the media, obtained from BL/6 cells containing 32 μg of antigenic human factor IX (determined by ELISA), was passed through the column. Nearly 3.5 μg of the biologically active material was recovered from the column. This represents over 10% of the total antigenic factor IX in the starting sample. No biologically active factor IX could be identified from uninfected MEF or BL/6 cells.

D. Detection of Human Factor IX in Mice

Figure 3:
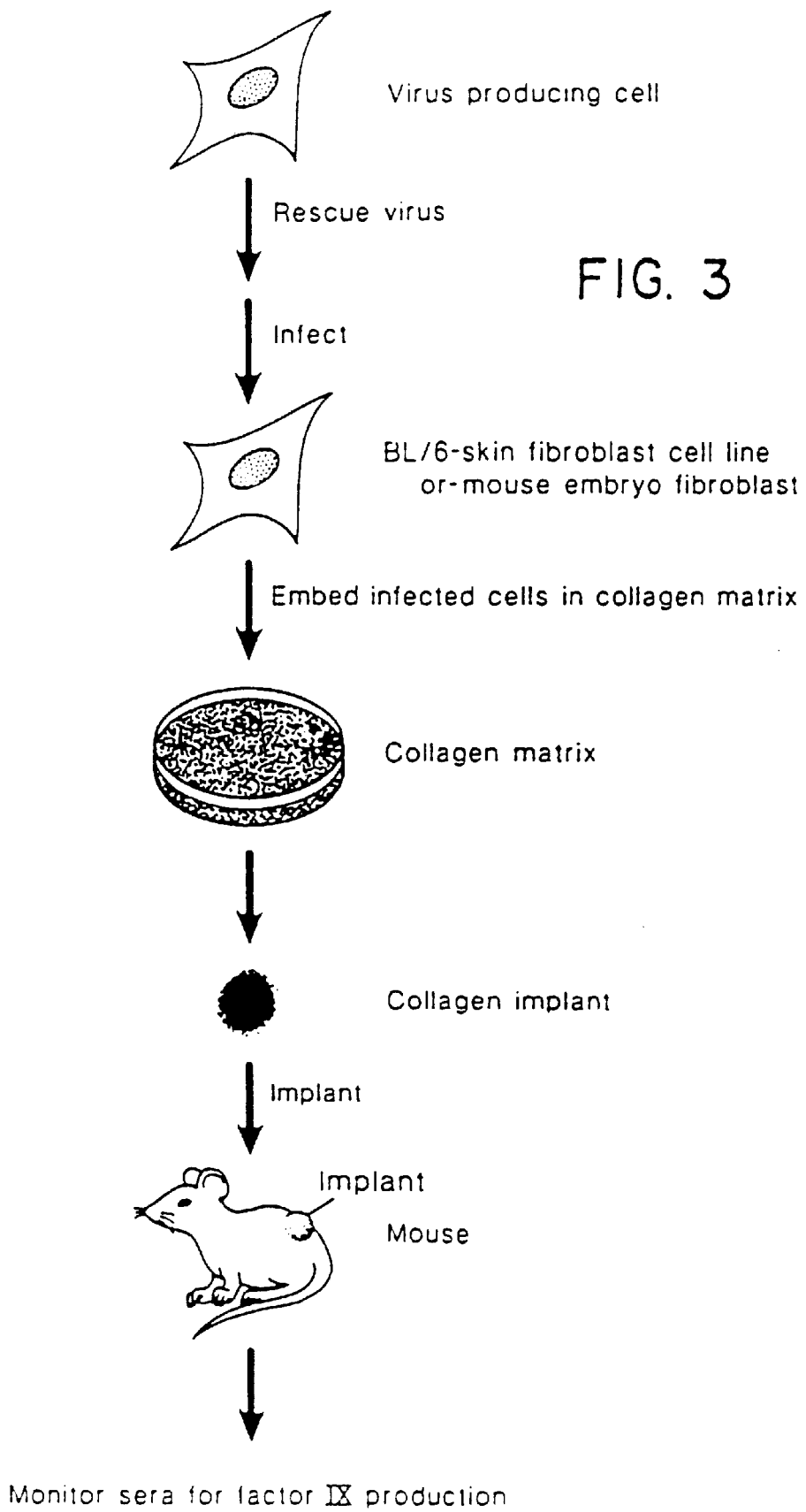
FIG. 3 is a schematic representation of the protocol used to generate and graft collagen implants into the loose connective tissue of the skin of a mouse.

Grafted with Infected Fibroblasts Infected MEF cells and BL/6 cells were cultured in an extracellular matrix, composed of collagen, before grafting. A tumor cell line, BL/6, was chosen in addition to MEF because it has an advantage in growth and vascularization and thus would increase our chances of detecting secreted factor IX in the sera. Attachment of the cells to the collagen resulted in a three-dimensional array of cells stacked on top of one another. After the primary fibroblast cells (MEF) or the tumor cell line BL/6 contracted in the collagen gel, the cells were grafted into the loose connective tissue of the mid-back dermis of a recipient syngeneic C57BL/6 mouse (FIG. 3; a schematic representation of the protocol used to generate and graft the collagen implants into the loose connective tissue of the skin of a mouse). The inserted implants were observed to be extensively vascularized by day 14. A similar extent of vascularization was also detected in 28 day implants.

The serum levels of the human clotting factor were measured in engrafted mice by ELISA over a 34 day period. The average levels of human factor IX in 3 mice progressively increased from 20 ng/ml at day 2 to a peak of 97 ng/ml 7 days after grafting the BL/6 cells into the mice. The 4 mice grafted with the infected MEF fibroblasts showed a similar pattern of increase in which an average peak of 25 ng/ml of factor IX was detected at day 9. This rise was followed by a rapid decline to near non detectable levels of serum human factor IX at day 16 in both the BL/6 and MEF grafts. A minor peak of factor IX was seen at day 20 in mice with either graft, which was followed by loss of any detectable factor IX antigen. In parallel experiments, $10^7$ infected BL/6 or MEF cells were injected directly into the peritoneal cavity of the recipient C57BL/6 mice. Serum levels of human factor IX in the injected animals followed a similar profile as that seen with the grafts.

E. Explanted Grafts Make Factor IX

The decline in serum levels of antigenic human factor IX in animals that were either grafted or injected i.p. was not associated with the necrosis of cells in the grafts. BL/6 cells in the collagen matrix grew as an aggressive tumor at the site of the graft. The tumor continued to grow until the animals were sacrificed at day 32. Mice with grafts containing infected MEF were visibly vascularized upon gross inspection until day 28, however, by day 120 the extent of vascularization was reduced but the implant was still viable. Additionally, cells explanted at various times during the course of the experiment produced factor IX when grown in culture. Table I reports the amount of antigenic factor IX secreted from cells explanted from grafts; tissue was explanted from the grafts at times indicated in the Table (post implantation), and were cultured in vitro; when cells were confluent medium was replaced; after 48 hr, levels of secreted factor IX secreted into the culture were assayed by ELISA.

TABLE I

| Days after Implantation | Collagen explants, ng/ml | |
|---|---|---|
| | BL/6 | MEF |
| 14 | 180 | 40 |
| 21 | 210 | 27 |
| 28 | 150 | 11 |

The explanted BL/6 cells grew well in culture and secrete antigenic factor IX at levels similar to that before grafting. The MEF cells explanted from the grafts at days 14 and 21 grew well in culture, but produced slightly lower levels of factor IX. Cells explanted at day 28 did not grow well, and the low level of factor IX secreted from these cells is perhaps a consequence of this poor growth.

F. Detection of Serum Anti-Factor IX Antibodies

To further investigate the decline of serum levels of human factor IX it was reasoned that the recipient animal mounted an immunological response against the highly immunogenic human factor IX protein. To test whether mice bearing grafts with infected BL/6 or MEF cells are generating anti-factor IX IgG antibodies, pooled serum samples were used to probe immunologic blots containing purified human factor IX protein. This was accomplished by subjecting purified human factor IX to PAGE under denaturing conditions and then transferring the PAGE separated protein onto nitrocellulose as described (Towbin, et al., 1979). The nitrocellulose strips were treated with blocking solution for 2 hr followed by 1:100 dilution of naive normal mouse serum; 1:100 dilution of mouse monoclonal anti-factor IX antibody FXC008; 1:100 dilution of serum from mouse harboring grafts containing infected MEF cells drawn at day 7, day 14, day 20, and day 28; and 1:100 dilution of serum from mouse harboring grafts containing infected BL/6 cells drawn at day 7, day 15, day 21 and day 29. After overnight incubation at 37° C. the strips were washed, incubated with $^{125}$I-labeled goat anti-mouse IgG antibody, and then subjected to autoradiography as described (Glenney, 1986).

The levels of anti-human factor IX IgG antibodies were not detectable in mice with MEF grafts at day 7 to day 21. Slightly higher levels of serum antibodies were detected in mice with BL/6 grafts during this period, presumably because they are releasing more factor IX. Maximum levels of anti-human factor IX antibodies were detected at day 28 in mice with either graft. The mice with BL/6 grafts exhibited the highest level of xeno-antibodies. Pooled serum drawn from mice 28 days after i.p. injection with infected MEF also showed anti-factor IX IgG antibodies albeit at much lower levels. Naive animals which have not been exposed to infected BL/6 or MEF cells do not make anti-human factor IX antibodies. These observations suggest that human factor IX is continuously produced in grafted mice but is not detectable due to a large pool of mouse anti-human factor IX antibodies.

G. Discussion of Results

This example describes the development and characterization of a new system for the delivery of a gene product into an animal. The BL/6 cells and MEF cells infected with a helper free recombinant retroviral vector containing the human clotting factor IX cDNA secrete biologically active clotting factor at a rate 10 fold higher than seen with another retroviral vector containing the human clotting factor cDNA (Anson, et al., 1987). In addition, the example demonstrates that those genetically modified cells can be reintroduced into the loose connective tissue of the dermis of a syngeneic mouse. Grafts are quickly vascularized in the presence of angiogenic factor, fibroblast growth factor, and remain vascularized for at least 28 days. Grafts containing the BL/6 cells grow as aggressive tumors over this period while the size of the grafts containing the MEF cells does not increase over the same period. The clotting factor secreted from the infected cells in the graft is accessible to the circulatory compartment and can easily be detected in serum of the graft recipient. Functional status of the infected cells in the grafts can be measured by monitoring serum levels of human factor IX or by the ability of explanted cells to continue secreting the human protein. However, C57BL/6 mice recognize the human blood clotting factor as foreign and thus mount a strong humoral immune response against it. Although a humoral response against factor IX clearly exists, there does not appear to be a major cell mediated response against the cells in the grafts. The cells in the graft are still viable after 28 days of implantation and continue to synthesize factor IX protein.

Even though the data presented here was obtained from mouse embryo fibroblasts, it should be noted that the observations have been extended by infecting adult hemophiliac dog fibroblasts with factor IX retrovirus.

It should also be noted that in normal individuals, levels of factor IX protein are approximately 5 µg/ml of plasma. Although the levels reported here are lower by several orders of magnitude, it should be remembered that individuals containing 0.5 µg of biologically active factor IX per ml in plasma do not show the symptoms of hemophilia. The low levels of factor IX can be increased either by making improved vectors capable of generating large amounts of factor IX proteins or, alternatively, by grafting more cells. According to the data presented here, up to 25 ng of factor IX per hr can be generated from an implant containing $4 \times 10^6$ cells. In larger animals multiple grafts of up to $10^8$ cells can be easily implanted, increasing the levels of factor IX protein to that required to alleviate the deficiency.

The efficiency of the invention delivery system can be further enhanced by such expedients as culturing infected cells in a defined medium (without fetal bovine serum) and applying improved technology for the reconstitution of living skin (Bell, et al., 1983). Moreover, improved surgical skills may ensure that the implant would lay flat in the dermal compartment of the mouse skin to allow more uniform vascular development and hence improve cell viability during the brief period required for vascularization. Although the extent of cell viability has not yet been determined in grafts containing MEF cells, experiments in rats have shown that transplanted fibroblasts persist for at least 13 months (Bell, et al., 1983).

In conclusion, this example has shown that skin fibroblasts can be used as a viable mode of introduction and expression of foreign genes in mammals. The process of manipulation of genetically engineered fibroblasts appears to be both less complex and cumbersome than the widely accepted use of bone marrow transplantation for somatic cell gene therapy. Example III

A. Animal and Cell Culture Conditions

Adult male C57 BL/6J mice (6–8 weeks old) and Nu/Nu athymic mice were obtained from the Jackson Laboratory, 600 Main Street, Bar Harbor, Me. The retroviral packaging cell line psi-CRE and psi-CRIP [Danos, 0. and Mulligan, R. C., Proc. Natl. Acad. Sci. USA 85: 6460–6464 (1988)] and the cell lines NIH 373 and rat 208 F were maintained in Dulbecco's Modified Eagle's Medium (DMEM) supplemented with 10% bovine calf serum. Primary fibroblasts were obtained from day-17 embryos of C57 BL/6J mice and were grown in DMEM supplemented with 10% fetal calf serum. Infected cells were selected in medium containing 400 µg/ml of G418.

B. Vector Construction

Retroviral vector LNCdF9L, which transduces canine factor IX, has previously been described [Axelrod, et al., Proc. Natl. Acad. Sci. USA 87: 5175–5177 (1990)]. The vectors shown in FIG. 4 were generated by inserting a 3.1 kBP BamHI fragment containing the entire coding sequence of the β-galactosidase gene into the BglII site plasmid LNL-SLX to generate the vector LNL-SLXβgal (in the Figure, the number of NEO$^R$ colonies examined is in parentheses; expression of β-galactosidase activity was determined by X-gal staining). The LNL-SLX vector is a derivative of LNL-XHC [Bender, et al., Virology 61: 1639–1946 (1987)] and contains a new polylinker to increase the number of cloning sites. A 350 bp HindIII fragment of the mouse dihydrofolate reductase (DHFR) promoter was cloned in the unique HindIII site of LNL-SLXβgal. A BamHI/HindIII fragment containing the human intermediate early Cytomegalovirus (CMV-IE) promoter [−522 to +55; Nelson, et al., Mol. Cell. Biol. 7: 4125–4129 (1987)] was cloned in the BamHI/HindIII site if LNL-SLXβgal.

C. Virus Production

Ten µg of plasmid DNA was transfected into the ecotropic packaging cell line psi-CRE by the calcium phosphate coprecipitation method. The medium was changed 24 hours later; and 48 hours after transfection, the culture medium was harvested and used to infect the amphotropic packaging cell line psi-CRIP in the presence of 8 µg/ml of POLYBRENE. Single colonies of infected psi-CRIP were isolated by selection in the presence of G418-containing medium and expanded. Recombinant retroviruses were harvested from confluent culture dishes, filtered and used to infect NIH 3T3 cells in the presence of POLYBRENE to determine the viral titers. Twenty-four hours after infection, the medium was changed to G418-containing medium and colonies were stained and counted after 12 to 14 days. The presence of helper virus was assayed by the marker residue method [Keller, et al., Nature (London) 318: 149–154 (1985)]. Briefly, the medium from the infected cells was used to infect naive NIH 3T3 cells. The presence of β-galactosidase positive.cells was determined after 72 hours and the presence of G418 resistant colonies was quantified after 14 days. Assays for production of Factor IX were carried out as described by Axelrod, et al., supra. The transduced fibroblasts produced ~400 ng of canine Factor IX/$10^6$ cells/day.

D. Implantation of Infected Mouse Embryo Fibroblasts in Mice

Infected mouse embryo fibroblasts were embedded in a collagen matrix as previously described [St. Louis and Verma, Proc. Natl. Acad. Sci. USA 85: 3150–3154 (May 1988)]. The collagen matrix containing $2 \times 10^6$ infected fibroblasts was then grafted into the connective tissue of the dermis in the mid-back of recipient mice. To ensure rapid vascularization of the grafted tissue, a 2mm$^2$ piece of gelfoam (Upjohn) containing 2 µg of basic fibroblast growth factor was inserted into the connective tissue along with each graft as previously described by St. Louis and Verma, supra. At different intervals of time, the implanted artificial collagen matrix was removed and stained for β-galactosidase activity.

E. Analysis of β-galactosidase Activity

Beta-galactosidase histochemistry was performed according to Sanes, et al., Embo. J. 5: 3133–3142 (1986), with minor modifications. Briefly, cultured cells were rinsed with phosphate buffered saline solution (PBS), pH 7.4, and then fixed for 5 minutes on ice in 2% formaldehyde plus 0.2% glutaraldehyde in PBS. The cells were then rinsed 2 times with PBS and overlaid with a solution containing 1 mg/ml of 4-Cl-5-Br-3-indodyl-β-galactosidase (X-gal), 5 mM potassium ferricyanide, 5 mM potassium ferrocyanide and 2 mM MgCl$_2$ in PBS, pH 7.4. Incubation was performed at 37° C. for 2 to 24 hours. To analyze β-galactosidase activity in the artificial collagen matrix, the fixation was prolonged for 30 minutes on ice.

F. Expression of Factor IX from Fibroblast Implants in Nude Mice

To address the potential problem of immune response against foreign proteins, the canine Factor IX infected syngeneic skin fibroblasts were implanted in nude mice. If transformed mouse fibroblasts producing canine Factor IX are used as an implant, the levels of Factor IX detected in mouse serum are observed to be at their highest at about day 5 post implantation, and by day 10 decline to near basal levels. However, by day 15 the levels of secreted Factor IX begin to increase and continue to increase thereafter. Because the implant contained tumorigenic cells which lead to the formation of palpable tumors, the increase in production of Factor IX reflects cell growth. However, the experiment clearly shows that the reduction of Factor IX levels by day 10 is not due to antibodies against canine Factor IX, since biologically active Factor IX can be detected even after 30–35 days.

In contrast, when primary Nu/Nu mouse fibroblasts were infected with canine Factor IX retrovirus, expression of Factor IX in plasma could not be detected 10–11 days post implantation. The cells were explanted after 10 days from the collagen matrices and grown in culture media containing G418 to remove cells which may have invaded the encapsulated matrix. Approximately 10 to 20% of the cells in the graft were G418 resistant. Analysis of Factor IX from the explanted cells showed the level of secretion to be similar to preimplanted cells, though they had matured considerably and had a reduced rate of division. These experiments suggested that the inability of the implants to produce and secrete Factor IX is not due to either the immune response or rejection of the implant. Due to the unavailability of perhaps specific growth factors, the CMV promoter is apparently unable to drive transcription of Factor IX cDNA. However, other epifactors (e.g., cell mass etc.) may also account for the increased expression of Factor IX. Results obtained using PCR analysis also indicate that the levels of Factor IX RNA in the implant precipitously declines and is undetectable in day 16 implants.

G. Use of Housekeeping Gene Promoters

Figure 4:
FIG. 4 shows the structure of retroviral vectors containing the β-galactosidase gene, titers of the recombinant retroviruses and expression of β-galactosidase activity.

It was next investigated as to whether sustained expression in implants is a function of the type of the promoter used to initiate the transcription of the foreign gene. Since CMV is an inducible promoter (and therefore may require actively growing cells for induction), a promoter used to maintain the constitutive levels of many housekeeping genes was tested for the expression of β-galactosidase. Therefore, retroviral vectors containing murine dihydofolate reductase gene promoter and the bacterial β-galactosidase gene as a reporter were constructed (FIG. 4). Clones producing high titre amphotropic recombinant viruses were selected by infecting NIH 3T3 cells, analyzed for β-galactosidase activity, and the presence of helper viruses. FIG. 4 shows that only a few clones producing greater than 5×10$^4$/ml neo$^R$ colonies could be identified, but the resultant recombinant viruses were stably propagated. The initial levels of β-galactosidase activity were higher in cells infected with LNL-SLX CMV β-gal virus (visible after 2 hrs of incubation) as compared to LNL-SLX DHFR β-gal virus (visible after 8–6 hrs of incubation). However, in a population of NIH 3T3 cells infected with LNL-SLX DHFR β-gal virus, nearly all the G418 resistant cells were positive for β-galactosidase activity. In comparison, infection with LNL-SLX CMV β-gal virus showed that only 50% of the G418 resistant cells were β-gal positive. No replication competent virus could be detected by marker rescue in any of the clones tested.

Figure 5:
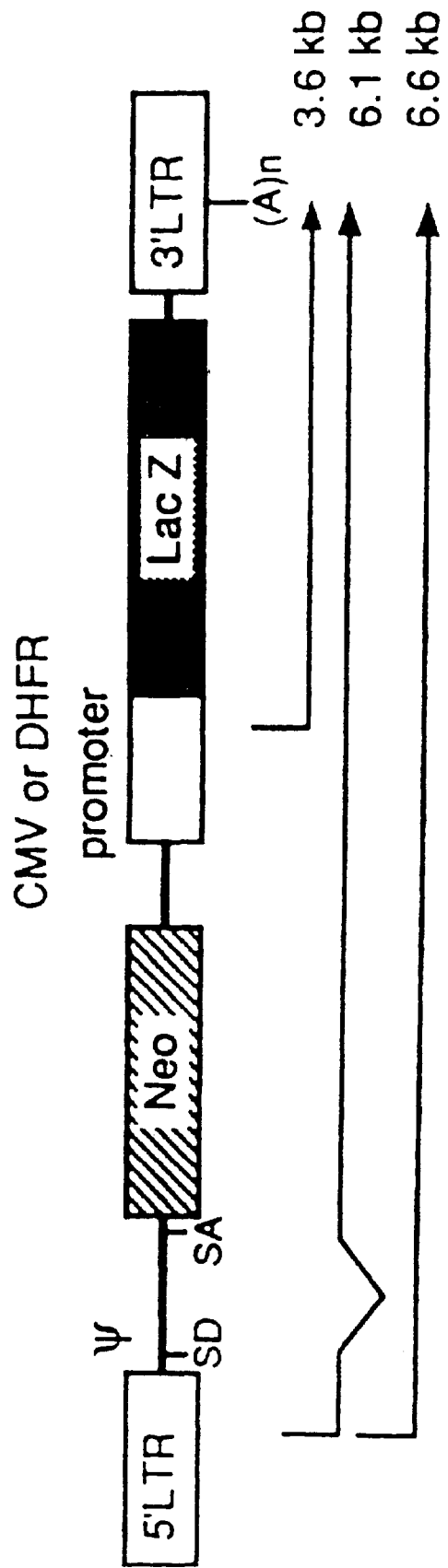
FIG. 5 shows the RNA transcripts made by the LNL-SLX CMV β-galactosidase and LNL-SLX DHFR β-galactosidase constructs.

To further characterize the recombinant viruses containing CMV and DHFR promoters, the RNA transcripts from cells infected with LNL-SLX CMV β-gal and LNL-SLX DHFR β-gal viruses were analyzed. FIG. 5 shows that transcripts of the expected size (6.6 kB, 6.1 kB and 3.6 kB) can be detected in virus producing CRIP cells or mouse embryo fibroblasts. The 3.6 kB mRNA represents transcripts initiated from the CMV or DHFR promoter. No detectable levels of β-galactosidase RNA were observed in uninfected cells.

H. β-galactosidase Expression in Mice

To test if the sustained expression of β-galactosidase can be attained in vivo, mouse embryo fibroblasts were infected with either LNL-SLX CMV β-gal or LNL-LSX DHFR β-gal viruses. The infected cells were then embedded in a collagen matrix and grafted in mice. After different time intervals, the grafts were explanted and analyzed for the presence of β-galactosidase positive cells. A minimum of two to three grafts were explanted at each time point. β-galactosidase positive cells (stained blue with X-Gal) could be detected in 10 day implants with both promoters tested. However, expression of β-gal was detected in animals for at least 60 days only when infected with LNL-SLX DHFR β-gal virus. It has thus been demonstrated that a housekeeping gene promoter like DHFR can provide sustained gene expression in the implants.

REFERENCES CITED IN THE SPECIFICATION

The following patent and journal publications are referred to in the specification. The contents and teachings of each of the publications are expressly incorporated by reference to be part of the present specification.

JOURNAL PUBLICATIONS

| | JOURNAL PUBLICATIONS |
|---|---|
| 1. | Anson, D.S., Choo, K.H., Rees, D.J.G., Gianelli, F., Goald, K., Huddleston, J.A., and Brownlee, G.G. (1984), EMBO J. 3:1053–1060. |
| 2. | Anson, D.S., Hock, R.A., Austen, D., Smith, K.J., Brownlee, G.G., Verma, I.M., and Miller, A.D. (1987), Mol. Biol. Med. 4:11–20. |
| 3. | Bajaj, S.P., Rapaport, S.I., and Maki, S.L. (1985), J. Biol. Chem. 260:11574–11580. |
| 4. | Bell, E., Ivarsson, B., and Merrill, C. (1979), Proc. Natl. Acad. Sci. USA 76:1274–1278. |
| 5. | Bell, S., Sher, S., Hall, B., Merrill, C., Rosen, S., Chamson, A., Asselinean, D., Dubertret, L., Coulomb, B., Capiere, C., Nusgens, B., and Nevewe, Y. (1983), J. Invest. Dermatol. 81:25–103. |
| 6. | Chavin, S.I. and Weidner, S.M. (1984), J. Biol. Chem. 259:3387–3390. |
| 7. | Dick, J.E., Magli, M.C., Huszar, D.H., Phillips, R.A., and Bernstein, A. (1985), Cell 42:71–79. |
| 8. | Elsdale, T. and Bard, J. (1972), J. Cell. Biol. 54: 626–637. |
| 9. | Ferlund, P. and Stenflo, J. (1983), J. Biol. Chem. 258:12509–12512. |
| 10. | Fournel, M.A., Newgren, J., Madanat, M. and Pancham, N. (1985), Thromb. Haemostasis 54:147. |

JOURNAL PUBLICATIONS -continued

11. Garver, R.I., Jr., Chytil, A., Courtney, M., and Crystal, R.G. (1987b), Science 237:762–764.
12. Garver, R.I., Jr.., Chytil, A., Karlsson, S., Fells, G.A.., Brantley, M.L., Courtney, M., Kantoff, P.W., Nienhuis, A.W., Anderson, W.F., and Crystal, R.G. (1987a), Proc. Natl. Acad. Sci. USA 84:1050–1054.
13. Glenney, J. (1986), J. Anal. Biochem. 156:315–319.
14. Goldsmith, J.C., Chung, K.S., and Roberts, H.R. (1987) Thromb. Res. 12:497–502.
15. Keller, G., Paige, C., Gilboa, E., and Wagner, E.F. (1985), Nature (London) 318:149–154.
16. Kreigler, M., Perez, C.F., Hardy, C., and Botchan, M. (1984), Cell 38:483–491.
17. Joyner, A., Keller, G., Phillips, R.A., and Bernstein, A. (1985), Retrovirus Transfer of a bacterial gene into haematopoietic progeniiot cells. Nature 305:556.
18. Ledley, F.D., Darlington, G.J., Hahn, T., and Woo, S.L.C., (1987), Proc. Natl. Acad. Sci. USA 84:5335–5339.
19. Ledley, F.D., Grenett, H.E., McGinnis-Schelnutt, M., and Woo, S.L.C. (1986), Proc. Natl. Acad. Sci. 83:409–413.
20. Mann, R., Mulligan, R.C., and Baltimore, D. (1983), Cell 33:153–159.
21. Miller, A.D. and Buttimore, C. (1986), Mol. Cell. Biol. 6:2895–2902.
22. Miller, A.D., Eckner, R.J., Jolly, D.J., Friedmann, T., and Verma, I.M. (1984), Science 225:630–632.
23. Miller, A.D., Law, M.F., and Verma, I.M. (1985), "Generation of Helper-Free Amphotropic Retroviruses that Transduce a Dominant-Acting, Methotrexate-Resistant Dihydrofolate Reductase Gene", Molec. Cell. Biol., 5(3):431–437.
24. Morgan, J.R., Barrandon, Y., Green, H., and Mulligan, R.C. (1987), Science 237:1476–1479.
25. Mulligan, R.C. (1983), "Construction of Highly Transmissible Mammalian Cloning Vehicles Derived from Murine Retroviruses, in Experimental Manipulation of Gene Expression, M. Inouye (ed), p. 155–173.
26. palmer, T.D., Hock, R.A., Osborne, W.R.A., and Miller, A.D. (1987), Proc. Natl. Acad. Sci. USA 84:1055–1059.
27. Selden, R.F. Skoskiewicz, M.J., Howie, K.B., Russell, P.S., and Goodman, H.M. (1987), Science 236:714–718.
28. Smith, K.J., Singaraju, C., and Smith, L.F. (1987), Am. J. Clin. Pathol. 87:370–376.
29. Sorge, J., Kuhl, W., West, C., and Beutler, E. (1987), Proc. Natl. Acad. Sci. USA 84:906–909.
30. Suttie, J.W. (1980), CRC Crit. Rev. Biochem. 8: 191–223.
31. Todaro, G.J. and Green, H.J. (1963), J. Cell. Biol. 17:299–313.
32. Towbin, H., Staehelin, T., and Gordan, J. (1979), Proc. Natl. Acad. Sci. USA 76:4350–4354.
33. Verma, I.M. (1985), Retroviruses for gene transfer. In Microbiology-1985 (ed. L. Leive et al.), p. 229. American Society for Microbiology, Washington, D.C.
34. Williams, D.A., Lemischka, I.R., Nathans, D.G., and Mulligan R.C. (1984), Nature (London) 310:476–480.
35. Wolfe, J.A., Yee, J.K., Skelly, H.F., Moores, J.C., Respess, J.G., Friedmann, T., and Leffert, H. (1987), Proc. Natl. Acad. Sci. USA 84:3344–3343.

PATENT PUBLICATIONS

1. PCT international Application, PCT/US85/01442, International Filing Date: 29 Jul. 1985; Applicant: The Salk Institute for Biological Studies; Inventors: I.M. Verma, A.G. Miller, and R.M. Evans; Title: Retroviral Gene Transfer Vector.
2. United States Pat. 4,624,944, issued Nov. 25, 1986 to the Regents of the University of California for "Human Seminal Alpha Inhibins".

SPECIFICATION SUMMARY

From the foregoing description, one of ordinary skill in the art can understand that the present invention is a new somatic cell gene therapy method. According to the invention, transduced fibroblasts are preferably created by infecting fibroblast cells in vitro with chimeric retroviruses that contain at least one functionally active "replacement gene", optionally under the additional control of a constitutive or inducible promoter other than the retroviral promoter. Such replacement genes can be either foreign genetic material that is not found in fibroblast cells, or native genetic material that is found in fibroblast cells but not normally expressed in biologically significant concentrations in these cells. Since the invention uses transduced fibroblasts from the individual or animal to be treated, the possibility of rejection is minimized. In addition, since the invention implants the transduced fibroblasts in the highly vascularized loose connective tissue of the dermis, the transduced cells, and thus their "replacement" gene products, have direct access to the circulatory system. As a result the needed replacement gene products can easily and efficiently be distributed to other parts of the body. When the gene therapy is no longer needed, the implanted fibroblasts can be conveniently removed.

Since the fibroblasts can be transduced to express a variety of replacement genes, the method of the invention has many important applications for both humans and animals. For example, the method can be used to treat diseases caused by genetic defects, to deliver drugs to individuals and animals, to induce immune response, and to administer birth control hormones.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A gene therapy method comprising:
   implanting in the loose connective tissue of the dermis of a subject, a collagen matrix containing transduced subject-derived primary fibroblasts, wherein said transduced fibroblasts are infected with a recombinant retroviral vector that comprises exogenous genetic material encoding a gene product, and wherein said transduced fibroblasts express said gene product.
2. A gene therapy method according to claim 1, further comprising:
   implanting an angiogenic substance in said loose connective tissue of the dermis, together with said matrix containing transduced fibroblasts.
3. A gene therapy method according to claim 2, wherein said angiogenic substance is fibroblast growth factor.

4. A gene therapy method according to claim 1, wherein said exogenous genetic material comprises at least one functionally active replacement gene.

5. A gene therapy method according to claim 4, wherein said functionally active replacement gene encodes at least one protein selected from blood clotting factors, hormones, enzymes, inhibitors or drugs.

6. A gene therapy method of claim 1, wherein expression of said gene product is under the control of a constitutive promoter.

7. A gene therapy method according to claim 1, wherein said fibroblasts are skin fibroblasts.

8. A gene therapy method according to claim 1, further comprising:

removing said implanted collagen matrix from the loose connective tissue of the dermis when gene therapy is no longer desired.

9. Transduced primary fibroblasts contained in a collagen matrix suitable for implantation into the loose connective tissue of the dermis of a subject, wherein said transduced fibroblasts are infected with a recombinant retroviral vector that contains exogenous genetic material encoding a gene product, wherein said transduced fibroblasts express said gene product, and wherein expression of said gene product is under the control of a constitutive promoter.

10. A method for immunizing a subject against immunogenic, exogenous material, said method comprising:

implanting in the loose connective tissue of the dermis of a subject, an extracellular collagen matrix containing transduced subject-derived primary fibroblasts, wherein said transduced fibroblasts are infected with a recombinant retroviral vector containing exogenous genetic material encoding an immunogenic gene product, and wherein said transduced fibroblasts express said gene product.

11. A method according to claim 10, further comprising:

implanting an angiogenic substance in said loose connective tissue of the dermis, along with said matrix containing transduced fibroblasts.

12. A method according to claim 11, wherein said angiogenic substance is fibroblast growth factor.

13. A method according to claim 10, wherein said immunogenic,exogenous genetic material encodes at least one immunogenic material selected from hormones, enzymes, inhibitors or drugs.

14. A method of claim 10, wherein expression of said gene product is under the control of a constitutive promoter.

15. A method according to claim 10, wherein said fibroblasts are skin fibroblasts.

16. A method according to claim 10, further comprising:

removing said implanted matrix from said subject when immunization is no longer desired.

* * * * *